United States Patent [19]

Lemonnier

[11] Patent Number: 4,640,777

[45] Date of Patent: Feb. 3, 1987

[54] MEMBRANE DEVICE FOR STERILITY TESTING

[75] Inventor: Jean Lemonnier, Le Vesinet, France

[73] Assignee: Millipore Corporation, Bedford, Mass.

[21] Appl. No.: 565,076

[22] Filed: Dec. 23, 1983

[30] Foreign Application Priority Data

Feb. 15, 1983 [FR] France .................................. 83 02391

[51] Int. Cl.$^4$ ............................................. B01D 13/00
[52] U.S. Cl. .............................. 210/433.2; 156/272.2; 210/445; 210/455
[58] Field of Search ............. 210/472, 445, 927, 433.2, 210/321.1, 455; 156/272.2; 29/163.5 F

[56] References Cited

U.S. PATENT DOCUMENTS

| 3,295,686 | 1/1967 | Krueger | 210/472 X |
| 3,932,153 | 1/1976 | Byrns | 210/445 X |
| 4,036,698 | 7/1977 | Bush et al. | 195/103.5 M |
| 4,054,523 | 10/1977 | Ingenito et al. | 210/927 X |

Primary Examiner—Frank Spear
Attorney, Agent, or Firm—Andrew T. Karnakis

[57] ABSTRACT

Apparatus for testing the sterility of fluids consisting of at least one hermetically sealed test container formed from a top portion, a bottom portion, a filter holder and a test filter. The filter is formed entirely from a hydrophilic material. The filter holder and test filter are welded to the top and bottom portions by a pressure-tight and vacuum-tight connection. Fluid is passed through the apparatus and through the test filter to deposit any microorganisms on the filter. Lateral bypass of fluid around the periphery of the test filter is eliminated.

10 Claims, 5 Drawing Figures

MEMBRANE DEVICE FOR STERILITY TESTING

BACKGROUND OF THE INVENTION

The present invention pertains to an apparatus for testing the sterility of fluids, notably antibiotics and other critical fluids, consisting of at least one hermetically sealed test container composed of a plastic material which is preferably transparent, with said container being connected under sterile conditions, by means of flexible connections and a cannula, to another container intended for samples, and/or to other containers for fluids. The top portion of each test container shall consist of a single element possessing the shape of a cup and outfitted with an inlet fitting, an air inlet, and, in the upper section, a built-in air filter. The bottom portion of the test container shall likewise consist of a single element outfitted with an attachment for draining, a mechanical holder for a microporous test filter, and an outlet attachment. The respective brims of both portions of the test container are to be welded together in a pressure-tight and vacuum-tight form, with the test filter being firmly mounted in an undetachable manner between the generally cylindrical lower brim of the top portion of the test container and the generally cylindrical upper brim of the bottom portion.

In medicine and in many other technical fields, maintaining absolutely sterile conditions for the items which are customarily employed and for any fluids which may be used often constitutes an indispensable requirement. This requirement, for example, is especially applicable with respect to solutions intended for perfusions being administered parenterally to patients in a direct form, as well as to instruments which are to be employed in providing perfusions. On account of the fundamental importance of ensuring sterility of instruments and fluids during use, it is necessary to perform sterility tests on a regular basis and to adhere to strict legally defined requirements during these tests (recommendations indicated by the pharmacopeiae of different nations). It has frequently been observed heretofore that, in testing sterility of antibiotics, particular difficulties arise on account of the specific properties of the pharmaceutical substances. Indeed, it has only been possible to overcome these difficulties by adopting highly elaborate precautions during completion of tests, as well as by performing a correspondingly higher number of individual tests.

In accordance with one research method which was widely employed in the past, fluids which were to be tested in terms of sterility were filtered in test containers composed of a transparent plastic material, with multiple sections (Consult Millipore Corporation printed text MRP-4, "Testing Sterility"). The aforementioned test containers possessed a cylindrical upper portion with a removable cap, with fittings for flexible connections and for an air filter cartridge being situated within the front wall. In turn, the bottom portion of each plastic container included a flat, ribbed filter-holder intended to provide support for a microporous membrane, with a fillet being situated upon the outer periphery, so that the bottom end of the top portion could be screwed into position. As a result of screwing the top portion into position, the microporous membrane could be firmly mounted between the holder and an annular shoulder within the top portion, with said shoulder being outfitted with a rubber toroidal joint. When testing for sterility was to be performed, fluids were poured into the top portion of a container under sterile conditions, after removal of the cap, and these fluids would subsequently flow through the microporous membrane when suction was applied. After filtering, the top portion of the container would be unscrewed under sterile conditions, and the center portion of the filter membrane would be removed, so that it could be placed in a bottle containing a culture medium for bacteria, the external ring of the filter being introduced into a bottle containing culture media for yeasts and molds, where incubation would take place at predetermined temperatures. This type of procedure was necessary on account of difficulties in terms of performing effective rinsing of the outer portion of the filter, which tended to retain products such as antibiotics, which inhibit bacterial growth.

This type of testing is relatively expensive, inasmuch as consistently sterile environmental conditions are required during the various phases, and there is a need for various externally performed procedures, such as screwing together the separate portions of the container, removing the filter membrane, cutting out a section of the membrane, and transferring this section to an incubation vessel. Moreover, highly experienced personnel are required. In addition, the individual portions of the test container are separated by joints, and it is possible for air to enter the container through these joints, thereby causing contamination. Furthermore, for extremely rigorous testing of antibiotics, the edges of filter membranes must be hydrophobic, in order to prevent traces of the antibiotic fluid which is being tested from adhering to the outermost edge of the filter, where it would be difficult to remove these traces of fluid by rinsing.

Recently, there has been widespread use of a sterility testing apparatus of the previously cited type (see U.S. Pat. No. 4,036,698, issued July 14, 1977), wherein two or three hermetically sealed test containers composed of a transparent plastic material are connected under sterile conditions to a cannula, by means of welded flexible connections and by means fo a flow divider. The cup-shaped top portion of each test container constitutes a single component, and its front wall contains an inlet fitting which is securely attached to a flexible connecting element, as well as containing an air inlet with a built-in, undetachable air filter. An annular flange is situated upon the bottom edge of the essentially cylindrical wall of the top portion of the test container. By means of this flange, the top portion of the container is firmly welded in a gas-tight and fluid-tight form to an annular flange situated at the top of the bottom portion of the container. A single component produced from a plastic material is also used to form the bottom portion of the container, which essentially comprises a tapered collecting funnel whose top side contains a series of radial ribs situated at angles, so as to furnish a flat holder for the filter membrane. These ribs extend into an outlet fitting situated a the center. A fundamental advantage of this particular testing apparatus in relation to prior types is derived from its constituting a pressure-right and vacuum-tight system which is self-enclosed, as well as being initially sterile. The apparatus consists of several hermetically sealed test containers which are interconnected by means of welded flexible connections, as well as being connected to a cannula by means of a flow divider. Because air can only enter individual containers through the microporous air filters situated within the front walls, it is possible to eliminate practically all errors attributable to secondary contamination when tests for sterility are being performed. Furthermore, this apparatus, for the first time, represents a means of providing pressurized filtration, so that fluids can be filitered by being introduced into containers under excess pressure, instead of by creating a vacuum within the outlet fitting situated at the center. Pressurized filtration renders it possible, for the first time, to achieve considerably more rapid completion of testing procedures, in addition to permitting practically absolute sterility during testing. After filtering of a predetermined quantity of a sample of a test fluid within multiple containers, it is possible to remove deposits and traces of the test fluid by introducing a sterile rinsing fluid into all of the containers simultaneously. Upon completion of rinsing, various culture media are then placed within the respective containers. This procedure can be performed easily, inasmuch as the cannula is inserted within the septum-seal of a vessel containing a culture medium, while conventional shut-off components can be used to seal the flexible connections extending from the flow divider to individual containers, in order to ensure that the culture medium shall only flow into the test container which has been selected for that purpose. Subsequently, incubation is permitted to occur at predetermined temperatures for a specific period of time, within the respective test containers filled with different culture media. A cap is employed for hermetic sealing of the outlet fitting situated at the center, and it is possible to remove a section of the previously sealed inlet connection in order that it may be placed over the air inlet so as to ensure hermetic sealing.

When this type of apparatus is employed to test the sterility of fluids, excellent results can be obtained with numerous types of media, and the necessary experimental procedures for performing tests are extremely simple and rapid. Nevertheless, the previously cited difficulties in terms of testing fluids containing antibiotic substances continue to be present. In fact, filter membranes are tightly fitted between the top and bottom portions of containers, along the outermost edges, with the two portions being joined to one another by welding. Inasmuch as welding is performed along the outermost edge of the membrane, or through the edge, this portion of the membrane is damaged, and small quantities of antibiotics may therefore accumulate within the area of contact between the membrane edge and the two portions of the container, so that it would only be possible to remove these traces by repeated rinsing. When incubation must continue for relatively long periods of time, minute traces of antibiotics may be carried to the center portion of the filter membrane, by means of diffusion, for example. Under these circumstances, bacterial growth would be inhibited, so that test results may be erroneous. As a means of overcoming these basic practical problems, containers with filter membranes which possess a relatively extensive hydrophobic periphery and a hydrophilic center portion have been used for testing antibiotics and similar substances. Nevertheless, production of filter membranes with a disc-like shape is laborious and expensive, because protracted diffusion processes constitute the only means to rendering the periphery hydrophobic. Furthermore, the filtration yield is reduced, even when filtration under pressure is performed, inasmuch as the hydrophobic periphery is practically fluid-tight and is not involved in the process of filtration.

Another disadvantage arising from use of a hydrophobic membrane periphery is attributable to the fact that oxygen can enter the container through the outlet section and can therefore travel by diffusion to the culture medium located above the filter membrane. This circumstance, during tests for the presence of certain types of bacteria, may affect the results which are obtained. During sterility testing for antibiotics and similar products, it is also absolutely essential for the filter membrane to rest upon the ribs of the filter-holder in a completely flat position, without bending. Indeed, bending contributes to retention of fluid, which cannot be easily removed by rinsing. When a pre-cut filter membrane is secured between the two portions of a container by direct sealing or welding techniques, pressure by the melted plastic material against the filter membrane generates internal radial stress which changes the shape of the filter membrane and produces undesirable bending within the membrane, before the edges of the membrane are firmly secured between the top and bottom portions of the container. In practice, loss of shape can be prevented by imparting sufficient stiffness to filter membranes, by adding stiff fibers to the materials used for producing filters. Although published sources indicate that, insofar as filtration techniques may be concerned, it is advantageous to employ biologically inert cellulose ester membranes with a thickness of 150 micrometers, it is not possible from a practical standpoint to use filter membranes of this type without adding fibers, inasmuch as these membranes do not possess sufficient thickness.

As it is possible to observe, the previously cited difficulties, which especially emerge during filtration of fluids containing antibiotic substances or other critical substances, are influenced by the means adopted for mounting or attaching the filter membrane between the two portions of the test container.

SUMMARY OF THE INVENTION

One of the purposes of the present invention is to provide an apparatus for testing the sterility of fluids, notably antibiotics and other critical fluids, whereby it shall be possible, with a simplified structure and with improved performance in terms of flow levels or filtration, to eliminate the previously cited difficulties and to achieve a significant reduction in factors which produce errors during sterility tests.

In accordance with the present invention, the outer edge of a microporous filter membrane which possesses the shape of a disc and is composed of a biologically inert polymer substance is sealed along its upper surface upon the top portion of a container in a pressure-tight and vacuum-tight manner, as a result of welding, whereas the bottom surface of the membrane is secured to the bottom portion of a container by means of another weld, without any damage to the membrane material in the area where the respective welds shall be situated and without permitting melted plastic material from the container to flow through the membrane in the area where welding is to be performed. Hence, it is necessary to ensure that no joints or gaps are situated between the membrane surfaces and the respective portions of the plastic container and to prevent melted plastic material from flowing beyond the inner walls of these portions, into the interior of the container, during welding, for reliably preventing minute quantities of antibiotics from being deposited or trapped within these particularly critical areas.

The present invention pertains to an apparatus for testing the sterility of fluids which differs from prior systems by virtue of the fact that the disc-shaped filter consists of an entirely hydrophilic filter membrane, with the bottom and top surfaces of the outer edge of said membrane being secured in a pressure-tight manner to respective portions of the container by means of welds which are placed perpendicularly to the inner walls of these portions of the container.

When a filter membrane is joined to the two portions of a container in this manner, with said portions being directly welded together and placed in a radial position in relation to the outer section of the filter membrane adjacent to respective annular flanges, it is possible to make use of completely hydrophilic filter membranes which do not possess the previously required hydrophobic border. Thus, the present invention permits the desired level of structural simplicity to be achieved. Inasmuch as the entire filter membrane is therefore involved in filtration processes, performance levels in terms of flow rates or filter yield under the same test conditions are approximately 40 percent higher in relation to units of the same type with containers possessing the same dimensions. This improvement in terms of required filtration periods decreases the possibility of adsorption of antibiotics by filter membrane, inasmuch as it is known that longer filtration periods correspond to increased adsorption of antibiotics by the membrane. It is also possible to eliminate the procedures required for producing the formerly indispensable hydrophobic peripheral area, and filter membranes possessing the shape of a disc can be produced from suitable strips of material by automated procedures. Thus, procedures for producing containers in accordance with the present invention embody significant simplification. Because the respective welds are limited solely to surfaces of the edge of a filter membrane and because melted plastic material from the container hardly enters the pores of the filter membrane, the material for the filter shall be subject to less stress during welding and sealing. It is therefore possible to eliminate rippling in sealed filter membranes, which was formerly a fundamental problem. This circumstance permits use of finer filter membranes, even though it was formerly practically impossible to use such membranes because they could not be easily handled in the form of pre-cut discs. It is no longer necessary to reinforce filter membranes, especially by adding fibers, and fluids can therefore flow more easily, with less absorption by the filter, inasmuch as it is known that adsorption phenomena decrease in relation to thinness of filter membranes.

DESCRIPTION OF PREFERRED EMBODIMENTS

According to one version of the method to which the present invention pertains, which is an especially appropriate method for producing sealed containers, either the lower or upper surface of the edge of the membrane is secured to one portion of the container by direct application of heat and pressure, without permitting appreciable flowing of the material comprising the container. The other surface of the membrane edge is then secured to the other portion of the container by means of another weld, which is obtained by permitting melted container material to flow from an area situated outside the membrane and to spread into the space situated between the membrane surface and the surface of the portion of the container where welding is being performed, while the membrane is already being held in place by the first weld. In this way, the weld which joins the first surface of the membrane edge to the corresponding portion of the container resembles fusion welding, whereby the edge of the filter membrane is immersed within plastic material which has acquired fluidity as a result of melting. In turn, the weld which joins the other surface of the membrane edge to the corresponding portion of the container is a weld where material from the container has flowed into the previously cited open area, from an external location.

One advantage of this technique for joining the membrane to both portions of the container in accordance with the present invention, which acquires even greater importance when a fine or unreinforced membrane is used, is that it is possible to stretch a strip of the membrane material prior to completing the first weld. Hence, it is possible not only to perform cutting of a membrane which has been stretched after completion of the first weld, but to ensure that the membrane periphery shall be capable of withstanding pressure from the melted plastic material while the second weld is being completed.

In order to permit bonding by means of an external flow, it is appropriate for the brim of one portion of the container to contain an annular wedge-shaped bead. This bead, which shall ultimately constitute an annular flange, occupies a radial position in relation to the outer section of the disc-shaped filter membrane, and it is the source of the melted material which shall flow into the open area in order to provide the second weld. In accordance with the present invention, the position, composition, and size of the aforementioned annular bead must be selected in a manner whereby the quantity of plastic material flowing into the open area shall be sufficient to form a suitable weld along the entire edge of the filter membrane, as far as the inner wall of the respective portion of the container, as well as providing suitable pressure-tight and vacuum-tight welding of the two portions of the container within areas outside the filter membrane.

In order to furnish mechanically durable support for extremely fine hydrophilic filter membranes and in order to prevent contamination which may originate from the undersurface of the filter, which is exposed to the external atmosphere, one especially interesting application of the present invention permits the bottom portion of the container to be drained through an annular channel which is directly perpendicular to the inner wall of the container. A series of short and narrow channels demarcated by supporting ribs extends beyond this point, toward another annular channel, with both annular channels being connected to the outlet fitting at the center by means of radial draining channels. By means of this particular configuration, it is possible to provide direct draining of fluids flowing along the inner walls of the container and passing through the peripheral portion of the filter membrane, according to the shortest possible trajectory, in the direction of the outlet fitting, so that stagnation does not occur within this critical area. This aspect is especially important in terms of pressurized filtration, inasmuch as an overpressure exists within the innermost area of the top portion of the container, whereas the section of the drainage line situated below the filter membrane remains under atmospheric pressure, which does not facilitate removal of fluids in the direction of the outlet fitting situated at the center.

In one method of producing containers for a testing apparatus designed in accordance with the present invention, both portions of the container must be produced separately by means of injection molding. The air filter and the bilateral mechanical supporting piece are then welded to the upper portion of the container, and the filter membrane is mounted between the two portions of the container, along their respective brims. For this purpose, the filter membrane must be placed upon the brim of one portion of the container, and the surface of the membrane edge situated opposite this portion is welded into its position by means of heat applied through the membrane, while a predetermined pressure is maintained. During a subsequent phase, the brim of the other portion of the container is welded to the other surface of the membrane edge by permitting melted plastic material to flow in a radial direction, toward the interior and toward the first portion of the container. For welding the second portion of the container to the surface of the membrane edge and to the first portion of the container, it is possible to apply heat to an annular bead located upon one portion of the container until melting occurs, so that during mounting of the two portions of the container, the resulting flow of melted material shall fill the space situated between the surface of the filter membrane and the respective portion of the container, thereby filling this area in its entirety.

Container production can be facilitated significantly by adopting automated means of completing individual steps and by permitting unrolling of the filter material from a strip placed above prefabricated portions of containers occupying suitable positions. It is possible to cut filter membranes from the aforementioned strip in the form of circular filter discs, before or after completion of the first weld, in order to ensure positioning of the filter membrane in a stretched condition. Subsequently, it is possible to complete the second weld by melting the annular bead and by allowing the melted plastic material to flow in a radial direction.

The subsequent detailed description of an example of application of the present invention is accompanied by drawings wherein:

DETAILED DESCRIPTION OF THE DRAWINGS

Figure 1:
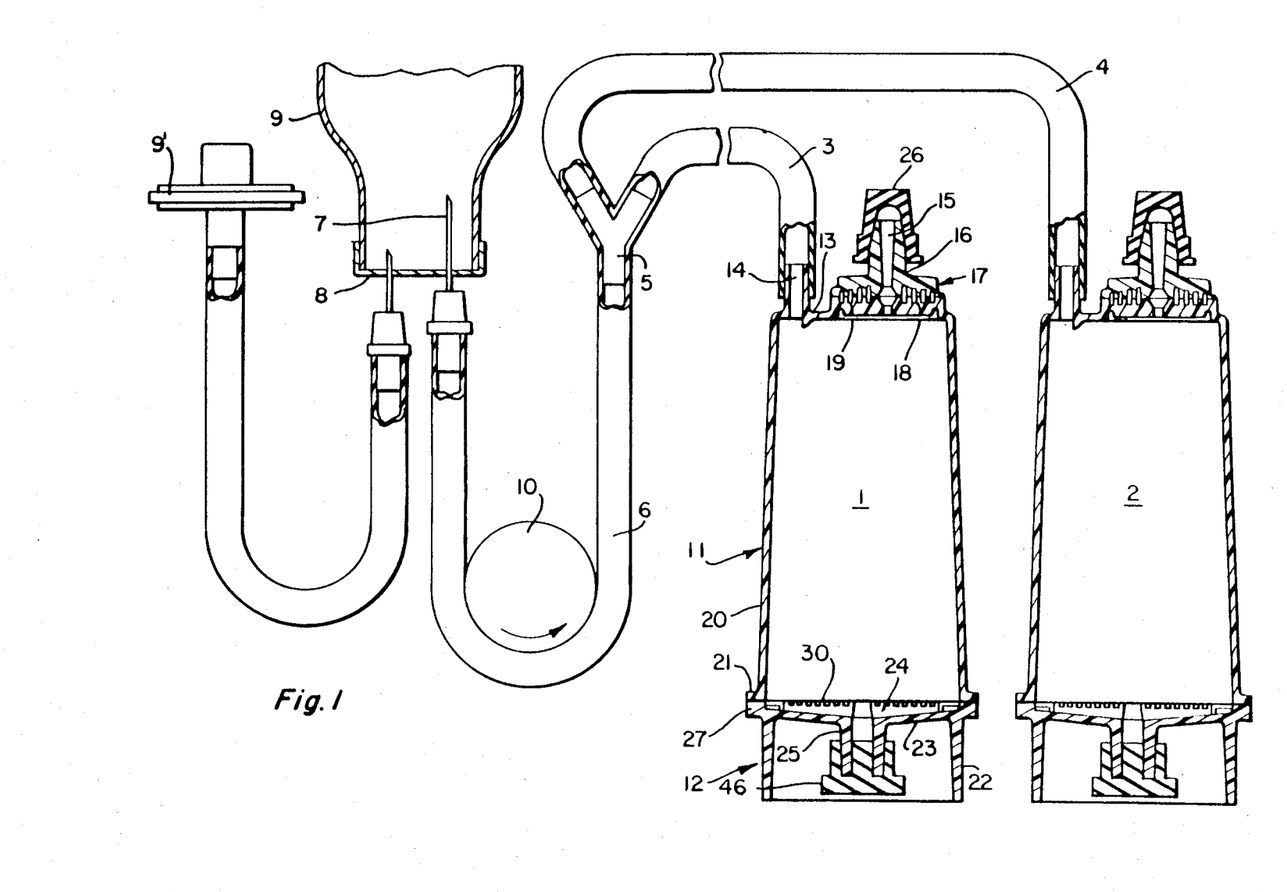
FIG. 1 indicates a sterility testing apparatus produced in accordance with the present invention, and it provides an axial view of two test containers.

The sterility testing apparatus appearing within FIG. 1 consists of two hermetically sealed test containers 1, 2 composed of a preferably transparent plastic material. These containers are respectively connected to a flow divider 5 by means of flexible connections 3, 4. The flow divider 5 shall be connected by a single flexible connection 6 to a cannula 7, which can be inserted through a cap 8 into a vessel 9 filled with a fluid intended for testing. As FIG. 1 indicates, another cannula which is connected by a flexible attachment to an air filter 9' is inserted into the aforementioned cap 8, in order to compensate for reduction of the volume of the fluid inside the vessel identified as 9. The fluid is carried to both test containers 1, 2 simultaneously by means of a tubular pump 10, through the flexible connections and through the flow divider, with an appropriate pressure being applied to the product which is to be filtered. In order to permit separate filling of the two test containers 1, 2 with different fluids, it is possible to employ a multiple-channel cock as a flow divider 5, or to use conventional clamps for selectively sealing the flexible connections 3, 4.

Each container 1, 2 consists of a single-piece top portion 11 and a single-piece bottom portion 12, which are firmly welded together in a pressure-tight and vacuum-tight manner. The top portion 11 possesses the shape of a cup, and the upper front wall 13 contains a built-in inlet fitting 14, as well as an air inlet 15 which is hermetically sealed by means of a rubber cap 26, as indicated in the drawing. The air inlet 15 constitutes a duct within the plastic cap 16 for an air filter 17, wherein one side of the microporous filter membrane 18 is supported along the upper surface 19 of the front wall by ribs which are demarcated by channels extending into the inner compartment of the top portion 11 of the container, whereas the other side is supported by the ribbed bottom portion of the filter cap 16. The periphery of the filter cap is welded in a gas-tight and fluid-tight form to the front wall of the container 13, so that, when the rubber cap is removed, air can only flow through the microporous filter membrane 18 in order to pass into or out of the inner portion of the container. A brim with a generally circular shape, which preferably consists of an annular flange 21, is situated at the bottom end of the slightly tapered wall 20 of the top portion 11. The top portion of the container is produced from a plastic material which is preferably transparent, in order to permit observation of the hues or opacity of fluids placed within the container.

The single-piece bottom portion 12 of the plastic container consists of a peripheral cylindrical brim 22, a drainage attachment in the form of a funnel 23, which preferably contains ribs 24 and an outlet fitting 25 at the center. In the version shown within the drawing, a plastic cap 46 is placed over the aforementioned fitting. Of course, the plastic cap 46 is removed from the outlet fitting 25 for each container 1, 2 during filtration. The upper end of the bottom portion 12 of the container possesses a generally circular brim which preferably consists of a annular flange 27 intended for permanent attachment to the annular flange 21 on the top portion 11 of the container by means of welding. A filter membrane 30, whose wall thickness is approximately 135 millimicrons±10 percent, or even less, rests in a flat position upon supporting ribs 24 within the bottom portion 12 of the container. The filter membrane is composed of a completely hydrophilic substance derived from a biologically inert polymer. The pore size for the microporous filter membrane is 0.45±0.02 micrometers, or an even smaller size.

Procedures for securing the membrane 30 within a container 1 or 2, which represent an essential characteristic of the present invention, shall be described hereinafter in relation to FIGS. 2a, 2b, and 3.

Figure 2A:
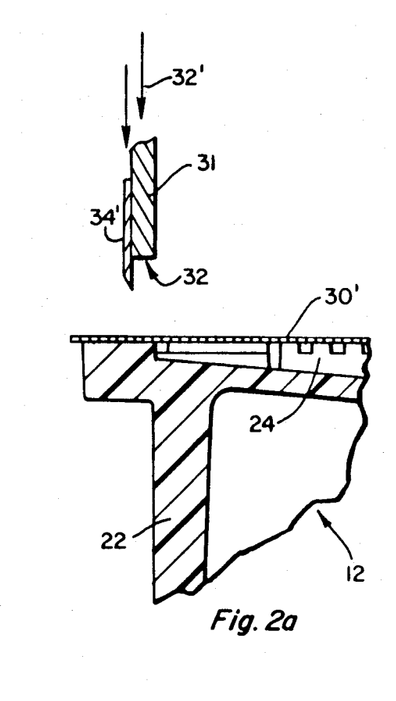
FIGS. 2a and 2b, as well as FIG. 3, provide enlarged views of two successive stages of production of a container, wherein both portions of the container are to be welded together.

Within FIG. 2a, a strip 30' of filter material placed under a predetermined level of stress is provided automatically by unrolling a roll of said material which does not appear within the drawing. The strip of material extends above bottom portions of containers placed in predetermined positions, and it is positioned in a perfectly flat manner. A hollow cylindrical welding tool 31 whose inner working surface 32 is heated to a precisely determined temperature by elements which do not appear within the drawing is moved forward in the direction of the arrow identified as 32'. The disc-shaped working surface 32 of the aforementioned welding tool 31 is designed so as to correspond precisely to the width of the edge 33 of a filter membrane which is to be secured by welding. The working surface 32 of the heated welding tool 31, which possesses the shape of an annular disc, is pressed against the strip 30' of filter material, and heat transmitted through an annular section of this strip is applied to the plastic material of the container portion located below the aforementioned section of the strip. By simultaneously pressing the strip against the heated area, it is possible to obtain a firm initial weld 34 between an annular section of the strip and the plastic material from the container portion 12 shown within FIG. 2b. The weld is situated beneath the brim 33. After the strip has been secured by gluing or by welding 34, an annular cutter 34' which is suitably positioned for vertical movement, outside the hollow cylindrical welding tool 31, travels downward, cutting the strip of filter material 30' directly outside and weld 34, so as to provide a disc-shaped filter membrane 30. On one hand, this technique ensures that the filter membrane 30 shall rest precisely upon the supporting ribs 24 during the welding procedure, and, on the other hand, it ensures prevention of slippage during the subsequent cutting procedure.

Figure 2B:
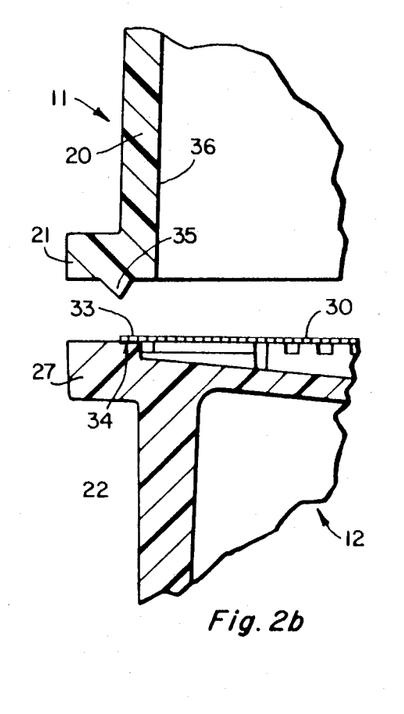
Figure 3:
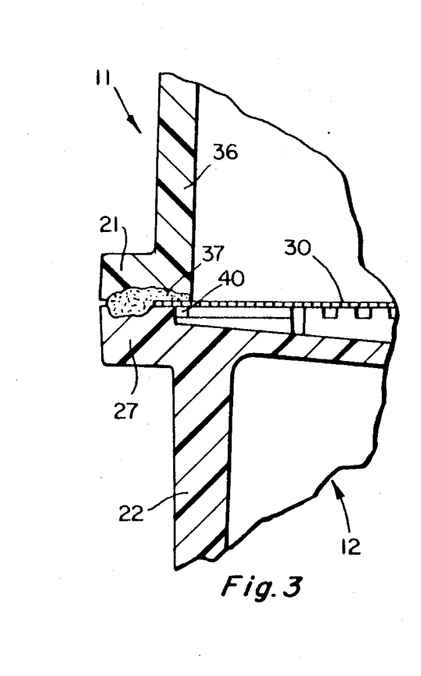

After the previously described procedures, the bottom portion 12 of the container and the filter membrane 30 which has been welded to the upper brim are placed in the position indicated within FIG. 2b, in order to permit welding of this portion to the top portion of the container. As it is possible to observe within FIG. 2b, the bottom brim of the top portion of the container contains a wedge-shaped annular bead 35 whose dimensions and position are particulary important in terms of completing the second weld 37 in accordance with the present invention. As shown within FIG. 2b, the tip of the wedge-shaped annular bead is situated slightly outside the peripheral portion of the edge 33 of the filter membrane. When the top portion 11 of the container is placed in contact with the bottom portion, the annular bead 35 must be heated in an appropriate manner, by ultrasonic means for example, to the melting temperature for the plastic material comprising the container. The heated tip of the annular bead 35 melts in contact with the plastic material for the bottom portion of the container, precisely alongside the peripheral portion of the membrane edge 33. As the top portion 11 of the container is gradually shifted toward the bottom portion 12, a portion of the plastic material from the annular bead 35 begins to flow inward in a radial direction and, as heat is constantly supplied, another portion of the plastic material from the annular bead begins to flow outward in a radial direction. In this way, it is simultaneously possible to produce a weld 37 between the upper surface of the membrane edge 33 and the top portion 12 of the container and a pressure-tight, vacuum-tight weld between both portions 11, 12 of the container. The annular bead 35 is situated upon the bottom brim of the top portion of the container in such a manner that, when the two portions 11, 12 of the container are placed in contact, the tip of the annular bead shall be brought into contact with the surface of the annular flange 27 for the bottom portion 12 of the container, in a radial position in relation to the outer portion of the filter membrane 30. In this way, it is possible to avoid excessive mechanical pressure upon the edge 33 of the filter membrane 30. In accordance with the present invention, the size and crosswise shape of the annular bead 35 must be selected in an appropriate manner for ensuring an adequate flow of melted plastic material precisely perpendicular to the inner wall of the container and for ensuring that plastic material from both portions 11, 12 of the container shall flow radially outside the edge 33 of the filter membrane 30, in order to provide an extremely durable weld which is gas-tight and liquid-tight. FIG. 3 indicates this set of conditions. During the previously described production procedures, it is essential to prevent impregnation of the edge 33 of the filter membrane 30 with plastic container material, so that the extremly fine pores of the filter membrane, which preferably extend through the membrane, shall only be sealed with plastic material along their open ends when the weld 34, 37 is formed. In this way, it is possible to prevent high mechanical stress from being applied to the especially fragile material comprising the filter membrane, so that fissures shall not develop within this material. The dimensions and position of the annular bead 35 must be capable of permitting a portion of the melted material from said bead to flow precisely perpendicular to the inner wall 36, when a weld 37 is being formed between the upper surface of the membrane edge 33 and the bottom brim of the respective portion 11 of the container. As a result, there are no gaps or accumulations of material where minute quantities of test fluids could collect and which could not be removed by repeated rinsing may ultimately collect. In addition, as a result of the two-step welding procedure in accordance with the present invention, the filter membrane 30 rests in a completely flat position upon the supporting ribs 24 within the bottom portion 12 of the container. Inasmuch as significant mechanical stress is not applied to the edges 33 of filter membranes during the two phases of welding, the filter membrane 30 is not affected by loss of shape or bending, which occur when a customary single-step technique is applied for welding the membrane to the container. Thus, it is not possible to make use of unstiffened or unreinforced membranes.

As a result of the present invention, it is possible to make use of substantially thinner filter membranes, and this aspect is of particular interest in relation to rinsing procedures which must be performed after filtration, inasmuch as adsorption by filter membranes diminishes in relation to reductions in thickness.

Figures 4, 5A, 5B, 5C:
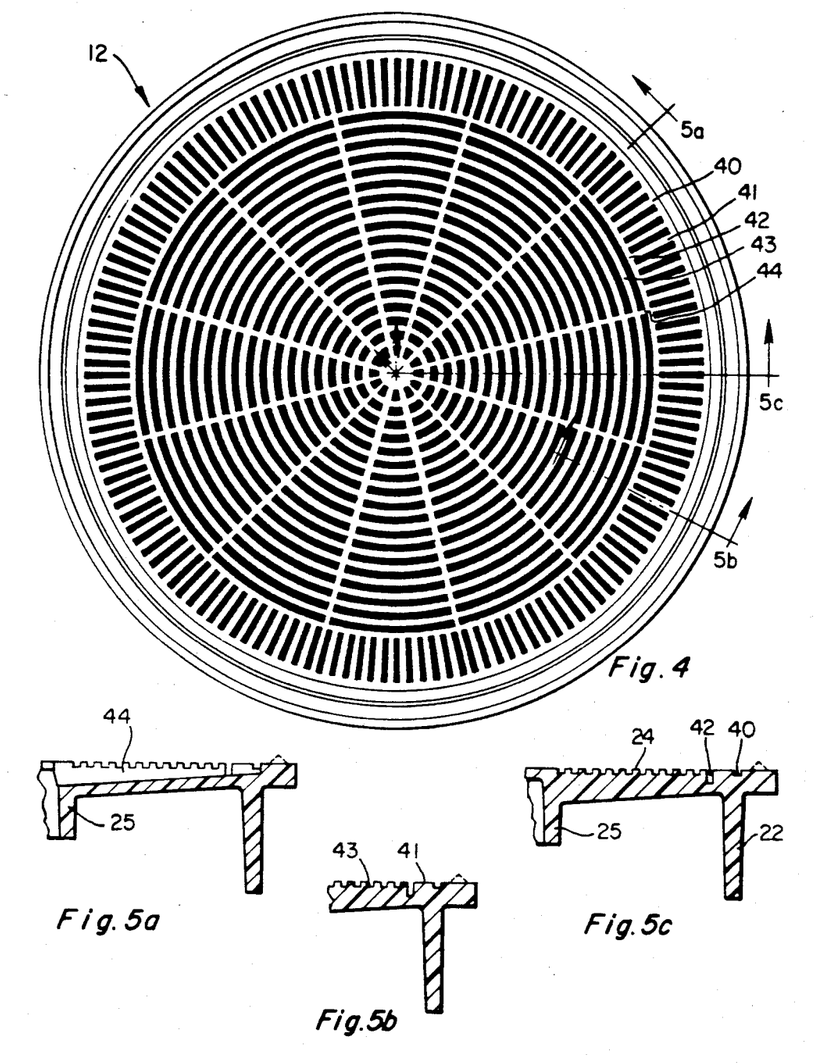
FIG. 4 is an overhead view of the bottom portion of a container and of the membrane holder, prior to assembly of the two portions of the container.
FIGS. 5a through 5c provide axial views of the bottom portion of the container, according to the dividing lines identified as 5a, 5b or 5c within FIG. 4.

FIG. 4 provides an overhead view of the bottom portion 12 of a container possessing drainage attachments and supporting ribs for hydrophilic filter membranes which have been provided in accordance with the present invention. The supporting ribs for the filter membrane 30 are represented by continuous lines, whereas channels for draining are represented by blank surfaces, constituting a peripheral area and a center area. As indicated in detail within FIGS. 5a through 5c, the peripheral area is demarcated by two concentric annular channels 40, 42 which are interconnected by multiple radial outlet channels 41, while the center area contains multiple concentric annular channels 43 which extend into radial drainage channels 44 arranged in a star configuration. These channels connect the annular channels 40, 42, and 43 to the outlet fitting 25 located at the center. The concentric annular channels are demarcated by the ribs 24 which provide support for the filter membrane 30. As a result of the series of radial channels 41 within the peripheral area, it is possible to ensure draining of this critical border area demarcated by the annular channels identified as 40 and 42 according to an extremely short trajectory. Hence, optimal removal of all liquids flowing within this area becomes possible.

On account of this particular combination of supporting components and drainage components, it is possible to obtain optimal rinsing of the peripheral area, which is always the most difficult area to rinse, as well as obtaining appropriate support for filter membranes, which can therefore be fine membranes which do not require reinforcement by means of fibers, for example.

Use of completely hydrophilic filter membranes 30 in accordance with the present invention, instead of conventional filter membranes possessing a hydrophobic peripheral area, offers still another advantage: during pressurized filtration, it is possible to maintain air pressure of approximately 29 psi above the filter membrane after a certain quantity of fluid has flowed into the inner compartments of the top portions 11 of containers, inasmuch as moistened hydrophilic materials for filter membranes are gas-tight up to a certain over-pressure level, which is approximately 3.36 psi for microporous materials of the cellulose ester type. When a rinsing fluid is introduced for example, it is no longer necessary to repressurize the inner portions of containers, inasmuch as pressure is constantly maintained. In contrast, rinsing or filling can take place under pressure, as soon as the respective fluids enter the inner portions of containers. Thus, by means of the present invention, testing periods can be significantly shortened.

The present invention is not restricted to the versions which have been described heretofore. For example, it is possible to perform pre-cutting of filter membranes 30 possessing the shape of round discs and to mount them within the bottom portions of containers individually, using manual or automatic means. In addition, it is not necessary for the annular bead 35 possessing a wedge-shaped cross-section to be formed upon the lower surface of the top portion of the container. It can also be formed upon the surface of the annular bead 27 for the bottom portion 12 of the container, provided that the proper position and shape are selected, as indicated by slanting lines within FIGS. 5a through 5c. In addition, it is possible for the holder for the filter membrane 30 to consist of a separate disc-shaped component with supporting ribs and drainage channels, which is to be inserted within the bottom portion of the container.

Lastly, in accordance with the present invention, it is possible for initial attachment of one of the surfaces of the edge 33 of the membrane 30 to a portion of the container by gluing or by welding to be performed within the top portion 11 of the container, instead of within the bottom portion 12, as specifically shown within FIG. 2b. Such a measure provides the advantage of ensuring tight welding along inner side of the container, without a need for regulating the flow of melted material originating from the annular bead 35 during completion of the second weld 37.

Although specific embodiments have been set forth in detail above, these are solely for the purpose of illustration as the invention is to be limited solely by the claims presented below.

I claim:

1. In an apparatus for testing the sterility of a fluid comprising at least one hermatically sealed test container wherein each of said containers comprises a top portion and a bottom portion sealed together and each of said containers have first and second ports in a first end thereof and a third port in an opposite end thereof, and each of said containers has a filter support member positioned within said container and spaced from said first end thereof and a first microporous membrane filter supported in a flat position on said filter support member, said first microporous membrane filter having an exposed area which is hydrophilic, said first membrane filter facing said first container end and being sealed about its entire periphery to annular flanges on said top portion and said bottom portion, said annular flanges extending from the interior of said container to a short distance outside said container, said first port including a second membrane filter having a pore size to screen any microorganisms above a predetermined size in a gas passing through said second membrane filter, means for introducing liquid into said container through said second port, means for collecting filtered liquid through said third port and means for capping said first port and said third port, the improvement which comprises said first membrane filter being entirely formed of a hydrophilic microporous material, said first filter membrane having an upper surface and a lower surface and an outer edge, one of the upper or lower surfaces adjacent said outer edge of said first membrane filter being sealed about its entire periphery to either said bottom portion or said top portion the other of said upper or lower surfaces being sealed to the other of said bottom or top portions, the bottom portion being sealed to the top portion about the entire outer edge of the first membrane filter, the portion of said first membrane filter being sealed to said top and bottom portions being substantially free of plastic material forming said top and bottom surfaces and wherein one surface of the first membrane filter is secured to one of the top portion or bottom portion of the container by means of an initial weld effected by direct application of heat and pressure, whereas the other surface of the edge of the first membrane filter is secured to the other of the top or bottom portion of the container by means of a second weld which is formed by a flow of melted container material originating from an area occupying a radial position, beyond the edge of the first membrane filter thereby forming a pressure tight and vacuum tight seal.

2. An apparatus in accordance with claim 2, wherein the melted container material which forms the second weld from a radially positioned area outside the first membrane filter is obtained from a wedgeshaped annular bead positioned upon an outer section of one portion of the container and constituting an annular flange.

3. An apparatus in accordance with any of claims 1, and 2, wherein the first membrane filter is composed of an entirely hydrophilic, unreinforced material having a thickness less than about 135 millimicrons±10 percent.

4. An apparatus in accordance with claim 1, wherein the filter support membrane includes a peripheral area demarcated by two concentric annular channels which are interconnected by multiple radial channels, as well as a center area containing multiple concentric annular channels which extend into radial drainage channels said radial drainage channels connecting said annular channels to a drainage attachment positioned at the center of said filter support member, said peripheral annular channel extending just to the edge of the inner walls of the top and bottom portions of the container.

5. A method of producing a container for testing sterility having a top portion and a bottom portion sealed together, and a first microporous membrane filter supported in a flat position on a filter support member, said first microporous membrane filter being formed entirely from a hydrophilic microporous material and being sealed about its entire periphery to annular flanges on said top portion and said bottom portion, said first filter membrane having an upper surface and a lower surface and an outer edge, the upper and lower surface adjacent said outer edge of outer said first membrane filter being sealed about its entire periphery to said bottom portion and said top portion to form a pressure tight and vacuum tight seal characterized by the fact that one of the upper or lower surfaces adjacent the outer edge of the first membrane filter is intially welded to the top or bottom portion of the container effected by direct applicaton of heat and pressure, the other of the upper or lower surfaces adjacent of the outer edge of the first membrane filter being fastened by a second weld to the other top or bottom portion of the container at the same time that the top and bottom portions of the container are welded together, said second weld being formed by melting a plastic bead on and extending about the circumference of said other portion of the container and adjacent the periphery of the first membrane, compressing said top and bottom portions of the contents to cause the melted plastic bead to migrate both toward and away from the interior of said container thereby sealing th first membrane to said top and bottom portion and cooling said melted bead to form a solid seal between the top and bottom portions.

6. A method in accordance with claim 5, wherein the first filter membrane is initially welded by providing heat through the edge of the first filter membrane with a specific level of pressure being applied.

7. A method in accordance with claim 6, wherein the second weld is formed by heating and melting a wedge-shaped annular bead, by ultrasonic means.

8. A method in accordance with any of the claims 5, 6 or 7, wherein the first membrane filter is formed from a continuous strip of filter material which is positioned in relation to a given portion of the container, with said strip being cut into a disc-shaped first membrane filter after one of the surfaces of the first membrane filter is secured to a portion of the container by means of an intitial weld.

9. A method in accordance with either of the claims 6 or 7 wherein the outer edge of the first membrane filter is initially welded to the bottom portion of the container.

10. A method in accordance with either of the claims 6 or 7 wherein the outer edge of the first membrane filter is initially welded to the top portion of the container.

* * * * *